US008845714B2

(12) United States Patent
DiMatteo et al.

(10) Patent No.: US 8,845,714 B2
(45) Date of Patent: Sep. 30, 2014

(54) SEALABLE ATTACHMENT OF ENDOVASCULAR STENT TO GRAFT

(75) Inventors: Kristian DiMatteo, Waltham, MA (US); John Spiridigliozzi, Sharon, MA (US); Robert C. Thistle, Bridgewater, MA (US)

(73) Assignee: LifeShield Sciences LLC, Plano, TX (US)

( * ) Notice: Subject to any disclaimer, the term of this patent is extended or adjusted under 35 U.S.C. 154(b) by 82 days.

(21) Appl. No.: 13/160,105

(22) Filed: Jun. 14, 2011

(65) Prior Publication Data

US 2011/0245906 A1 Oct. 6, 2011

Related U.S. Application Data

(63) Continuation of application No. 10/438,409, filed on May 15, 2003, now abandoned.

(51) Int. Cl.
*A61F 2/06* (2013.01)
*A61F 2/07* (2013.01)
*A61F 2/90* (2013.01)

(52) U.S. Cl.
CPC ........... *A61F 2/07* (2013.01); *A61F 2220/0058* (2013.01); *A61F 2/90* (2013.01); *A61F 2002/075* (2013.01); *A61F 2002/065* (2013.01); *A61F 2220/0075* (2013.01); *A61F 2220/005* (2013.01)
USPC ....................................................... 623/1.13

(58) Field of Classification Search
USPC ........... 623/1.15, 1.23–1.25, 1.27, 1.35, 2.11, 623/1.26, 2.17, 1.36, 1.16
See application file for complete search history.

(56) References Cited

U.S. PATENT DOCUMENTS

| | | | |
|---|---|---|---|
| 3,479,670 A | 11/1969 | Medell | |
| 3,870,675 A | 3/1975 | Kusayama et al. | |
| 3,953,566 A | 4/1976 | Gore | |
| 4,044,404 A | 8/1977 | Martin et al. | |
| 4,047,252 A | 9/1977 | Liebig et al. | |
| 4,304,010 A | 12/1981 | Mano | |
| 4,323,525 A | 4/1982 | Bornat | |
| 4,652,263 A | 3/1987 | Herweck et al. | |
| 4,655,771 A | 4/1987 | Wallsten | |
| 4,878,908 A | 11/1989 | Martin et al. | |
| 4,892,539 A | 1/1990 | Koch | |
| 5,108,424 A | 4/1992 | Hoffman, Jr. et al. | |
| 5,116,360 A | 5/1992 | Pinchuk et al. | |
| 5,151,105 A | 9/1992 | Kwan-Gett | |
| 5,163,951 A | 11/1992 | Pinchuk et al. | |
| 5,192,310 A | 3/1993 | Herweck et al. | |
| 5,304,197 A | 4/1994 | Pinchuk et al. | |

(Continued)

FOREIGN PATENT DOCUMENTS

| | | |
|---|---|---|
| EP | 1086665 | 3/2001 |
| EP | 1325716 | 7/2003 |
| EP | 1325717 | 7/2003 |
| WO | 00/69367 | 11/2000 |

*Primary Examiner* — Thomas McEvoy
(74) *Attorney, Agent, or Firm* — Vidas, Arrett & Steinkraus

(57) ABSTRACT

An endovascular prosthesis of the present invention includes an expandable stent and a means for sealably attaching a tubular graft to the stent within the stent's lumen. The means of sealably attaching a graft includes membranes, foams, polymeric materials and combinations thereof. Additionally, the present invention includes methods of forming an endovascular prosthesis and methods of implanting an endovascular prosthesis within a vessel to provide sealable securement of a tubular graft within the stent's lumen.

15 Claims, 15 Drawing Sheets

(56) References Cited

U.S. PATENT DOCUMENTS

| | | |
|---|---|---|
| 5,370,682 A | 12/1994 | Schmitt |
| 5,413,598 A | 5/1995 | Moreland |
| 5,476,506 A | 12/1995 | Lunn |
| 5,571,170 A | 11/1996 | Palmaz et al. |
| 5,632,772 A | 5/1997 | Alcime et al. |
| 5,639,278 A | 6/1997 | Dereume et al. |
| 5,653,705 A | 8/1997 | de la Torre et al. |
| 5,800,510 A | 9/1998 | Schmitt |
| 5,879,320 A | 3/1999 | Cazenave |
| 5,885,598 A | 3/1999 | Knauf et al. |
| 5,910,168 A | 6/1999 | Myers et al. |
| 5,911,753 A | 6/1999 | Schmitt |
| 5,913,894 A | 6/1999 | Schmitt |
| 5,916,264 A | 6/1999 | Von Oepen et al. |
| 5,931,865 A | 8/1999 | Silverman et al. |
| 5,948,018 A | 9/1999 | Dereume et al. |
| 5,976,192 A | 11/1999 | McIntyre et al. |
| 6,001,125 A | 12/1999 | Golds et al. |
| 6,019,786 A | 2/2000 | Thompson |
| 6,090,137 A | 7/2000 | Schmitt |
| 6,123,723 A | 9/2000 | Konya et al. |
| 6,159,239 A | 12/2000 | Greenhalgh |
| 6,214,036 B1 | 4/2001 | Letendre et al. |
| 6,221,099 B1 | 4/2001 | Andersen et al. |
| 6,261,257 B1 | 7/2001 | Uflacker et al. |
| 6,270,525 B1 | 8/2001 | Letendre et al. |
| 6,290,731 B1 | 9/2001 | Solovay et al. |
| 6,309,413 B1 | 10/2001 | Dereume et al. |
| 6,312,462 B1 | 11/2001 | McDermott et al. |
| 6,319,279 B1 | 11/2001 | Shannon et al. |
| 6,325,819 B1 | 12/2001 | Pavcnik et al. |
| 6,325,822 B1 | 12/2001 | Chouinard et al. |
| 6,331,188 B1 | 12/2001 | Lau et al. |
| 6,344,052 B1 | 2/2002 | Greenan et al. |
| 6,344,056 B1 | 2/2002 | Dehdashtian |
| 6,361,556 B1 | 3/2002 | Chuter |
| 6,379,373 B1 | 4/2002 | Sawhney et al. |
| 6,454,796 B1 | 9/2002 | Barkman et al. |
| 6,468,660 B2 | 10/2002 | Ogle et al. |
| 6,478,817 B2 | 11/2002 | Schmitt et al. |
| 6,524,336 B1 | 2/2003 | Papazolgou et al. |
| 6,585,756 B1 | 7/2003 | Strecker |
| 6,942,692 B2 | 9/2005 | Landau et al. |
| 2001/0039450 A1 | 11/2001 | Pavcnik et al. |
| 2002/0058987 A1 | 5/2002 | Butaric et al. |
| 2002/0096246 A1 | 7/2002 | Sennet et al. |
| 2003/0070682 A1 * | 4/2003 | Wilson et al. ............ 128/207.16 |
| 2003/0100944 A1 | 5/2003 | Laksin et al. |
| 2003/0130725 A1 | 7/2003 | DePalma et al. |
| 2003/0209835 A1 | 11/2003 | Chun et al. |

* cited by examiner

SEALABLE ATTACHMENT OF ENDOVASCULAR STENT TO GRAFT

CROSS-REFERENCE TO RELATED APPLICATIONS

This Application is a continuation of application Ser. No. 10/438409 filed May 15, 2003.

FIELD OF THE INVENTION

The present invention relates to an endovascular prosthesis for intraluminal delivery, and a method of implanting the endovascular prosthesis for repairing an aorta. More particularly, the present invention relates to endovascular prosthesis including a stent and a means for sealably attaching a graft thereto for use in a blood vessel or a bifurcated system, such as an abdominal aortic artery where it bifurcates to the common iliac arteries.

BACKGROUND OF THE INVENTION

An abdominal aortic aneurysm ("AAA") is an abnormal dilation of the arterial wall of the aorta in the region of the aorta that passes through the abdominal cavity. The condition most commonly results from atherosclerotic disease. Abdominal aortic aneurysms are typically dissecting aneurysms, which are aneurysms that are formed when there is a tear or fissure in the arterial lining or wall through which blood is forced and eventually clots, forming a thrombosis which swells and weakens the vessel. Abdominal aortic aneurysms typically do not cause pain and are easily detected by physical examination. The aneurysm may rupture if it is not detected and treated, causing massive hemorrhaging which is likely to be fatal to the patient.

Treatment of AAAs typically comprises some form of arterial reconstructive surgery, commonly referred to as a "triple-A" procedure. One such method is bypass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished.

Many patients experiencing such AAAs, however, are over 65 years of age and often have other chronic illnesses which increase the risk of pre-operative or post-operative complications. Thus, such patients are not ideal candidates for triple-A procedures. Further, this procedure is generally not performed successfully once an aneurysm has ruptured due to the extensiveness of the surgery and the time required to prepare a patient for surgery. The mortality rate for patient experiencing such ruptured aneurysms is over 65%.

As a result of the aforementioned disadvantages to conventional surgical methods, minimally invasive techniques have been developed for the repair of AAAs. Such methods involve placement of a stent-graft at the site of the aneurysm by a catheter, known as an introducer, which serves as a deployment device. The stent-graft and its deployment system are typically introduced into the blood stream percutaneously and negotiated by means of a guidewire to the site of the aneurysm where the stent is caused to be radially expanded. Such procedures are desirable as they can be performed using local anesthesia and do not expose the patient to many of the same risks associated with triple-A procedures. But the bifurcated structure and environment of the abdominal aortic and the technology of the prior art stent-grafts continue to be plagued with issues associated with long term stability.

In such minimally invasive repair procedures, the bifurcated structure of the abdominal aortic arch necessitates the use of a uniquely-structured bifurcated stent-graft. Typically, aneurysms, occlusions or stenoses will occur at the location where the aortic arch bifurcates into the iliac arteries and may also occur at the iliac arteries. The in situ positioning of stent-grafts in this area is more difficult than the positioning of such devices in the lumen of non-bifurcated vessels. As both limbs of a bifurcated stent-graft are inserted and advanced through a single branch of the femoral arterial system, one of the limbs of the stent-graft must ultimately be pulled or drawn into the contralateral branch so that the stent-graft is suitably positioned across both the aortic aneurysm and the associated common iliac aneurysms to supply circulation to each of the lower limbs.

Bifurcated stent-grafts are frequently too bulky to advance through a single iliac artery, particularly in view of the fact that the limb for the contralateral branch of the stent-graft must be inserted together with the limb of the ipsilateral branch. Additionally, care must be taken to not twist or kink the stent-graft as it is placed in the contralateral artery. The caudal portion of the graft must not stretch across the mouth of the internal iliac artery which would result in inadvertent occlusion of that artery. The procedure of drawing one limb of the stent-graft from one femoral artery to the contralateral femoral artery requires placement of a cross-femoral catheter using a closable wire basket prior to insertion of the stent-graft.

This procedure requires significant and skillful wire catheter manipulation, frequently within the aneurysmal cavity. As such, care must be taken to avoid disturbing or dislodging thrombic or embolic material from within the aneurysmal sac. Additional factors such as the severe tortuosity of the iliac arteries and the marked angulation of the aortoiliac junction resulting from the tendency of the abdominal aortic artery to extend caudally during aneurysm formation combine to make deployment of endoluminal bifurcated grafts time consuming and at increased risk of procedural complications and failure.

To overcome the aforementioned risks associated with the use of one-piece stent-grafts in the repair of aneurysms occurring in bifurcated vessels, two component bifurcated designs have been developed which may be assembled in situ. The first component consists of the upper trunk, which is positioned just below the renals, a stump, and an iliac limb. The second component is then deployed into the stump, connecting the device to the contralateral iliac limb. These devices have had a number of issues, which include fabric wear, kinking, and endoleaks at the upper neck and at the stump junction; in addition, some have proven to be difficult to manufacture, not secure to vessel wall, or difficult to assemble in situ.

The main reason for lack of success with endoluminal repair focuses around the fact that the vascular system in general, and more apparent in an aneurysm sac is the morphology continues to change. The morphological environment leads to unexpected and unanticipated stress which is placed on the stent-grafts used to treat the disease. Such wearing and endoleaking necessitates the repair of these devices, requiring additional surgical procedures which may include replacement of the device. Consequently, there is a continuing need for the development of stents with attached grafts and techniques useful for the repair of aneurysms in general, and AAAs.

SUMMARY OF THE INVENTION

In view of the foregoing, it is an object of the present invention to provide an endovascular prosthesis and method of implanting the prosthesis into a vessel that provides a means for sealably attaching a tubular graft within the endovascular prosthesis. Additionally, the present invention provides for a prosthesis that is flexible and durable to adjust to the morphological environment and is able to assemble in situ.

The present invention includes an endovascular prosthesis including an expandable stent having an inner lumen, and a means for sealably attaching a tubular graft within the lumen of the stent. The means of sealably attaching a graft includes membranes, foams, polymeric materials and combinations thereof.

Another embodiment of the present invention, there is provided an endovascular prosthesis including an expandable stent and a membrane supported by the stent and extending across the lumen. The membrane further including a graft receiving member for sealably receiving at least one tubular graft therethrough.

The present invention further provides an endovascular prosthesis as above-described and the membrane further including an electrostatically spun material having a graft receiving opening for sealably receiving at least one tubular graft therethrough.

An embodiment of the present invention, there is provided a bifurcated endovascular prosthesis including a first prosthetic component and a second component. The first component is similar to those described-above including a stent, a membrane extending transversely across the inner lumen of the stent and attached thereto. The membrane additionally having an opening. The second prosthetic component being extended through the opening in a substantially fluid tight seal. The second component further including one or more grafts.

A further embodiment of the present invention, there is provided a multi-component endovascular prosthetic system including two prosthesis and a tubular graft. Each prosthesis including an expandable stent and a membrane extending transversely across the inner lumen and attached to the stent. Each membrane further having a graft receiving opening. The tubular graft being extended sealably through a graft receiving opening of each prosthesis for directing fluid through the tubular graft.

Another embodiment of the present invention, there is provided an endovascular prosthesis including a stent having an inner lumen, a distal end and a proximal end, the distal end having an opening, and the proximal end having two openings opposing the distal opening; and a puncturable membrane extending across each of the proximal end openings.

Another aspect of the present invention, there is provided an endovascular prosthesis including an expandable stent, a first graft and a second graft. The expandable stent has a distal end and a proximal end, and an opening extending therethrough. The first graft being attached to the distal end of the stent within the opening, and having an inner lumen extending therethrough. The second graft being attached to the proximal end of the stent within the opening and spaced from the first graft. The second graft having at least two inner lumens extending therethrough and a membrane extending transversely across each of the inner lumens of the second graft.

Another embodiment of the present invention, there is provided an endovascular prosthetic assembly including an expandable stent and a tubular graft inserted within the inner lumen of the stent. The graft having an expanded foam attached to the exterior surface of the graft. The expandable foam sealably securing the tubular graft to the stent.

One aspect of the present invention, there is provided a kit of parts for assembly into an endovascular prosthetic system. The kit including an expandable stent for insertion into a body endovascularly; a tubular graft adapted to be inserted within the stent, the tubular graft having an interior surface for body fluid flow and an exterior surface; and an expandable foam on the exterior surface of the tubular graft. The expandable foam being adapted to expand within the stent to sealably secure the tubular graft to the stent.

A further embodiment of the present invention, there is provided an endovascular prosthetic assembly including a stent, a tubular graft extending into the stent and a polymeric material sealably supporting the tubular graft to the stent.

Another aspect of the present invention there is provided, a kit of parts for assembly into an endovascular prosthetic system. The kit including a stent having a primary reactive material being disposed on the inner surface of the stent; a tubular graft adapted to extend within the inner lumen, the graft having the primary material being disposed on the exterior surface; and a secondary material reactive with the primary material. The second material being adapted to be applied to the primary material upon insertion of the graft within the inner lumen, the secondary material being reactive with the primary material to form a seal between the graft and the stent.

A further aspect of the present invention there is provided methods of forming and methods of implanting the various endovascular prosthesis of the present invention within a vessel.

DETAILED DESCRIPTION OF THE INVENTION

The present invention relates to an endovascular prosthesis for intraluminal delivery, as shown in FIGS. 1-21. The prosthesis is particularly suited for use as a vascular prosthesis. The prosthesis of the present invention overcomes the aforementioned problems of the prior art including leaking and wearing between a tubular prosthesis and a stent. Additionally, the prosthesis of the present invention provides flexibility to adapt to the morphology of the vascular environment. The prosthesis of the present invention includes minimal components to provide for a simple assembly in situ.

Figure 1:
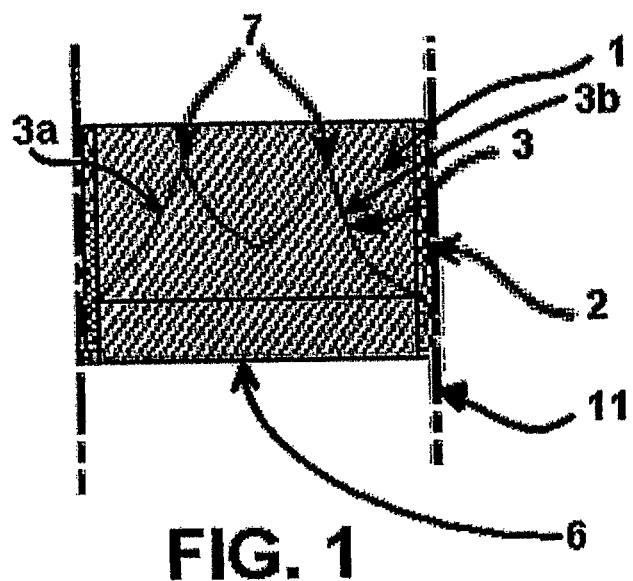
FIG. 1 is an enlarged plan view of the endovascular prosthesis of the present invention including a stent and attached membrane having graft receiving members.
Figure 3:
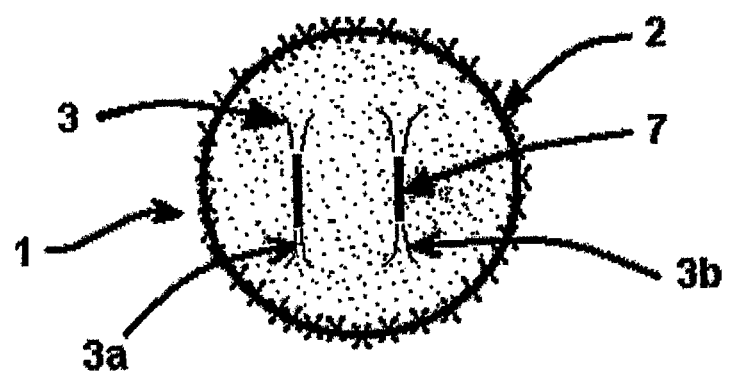
FIG. 3 is a top view of the endovascular prosthesis of FIG. 1 showing the graft receiving members.
Figure 2:
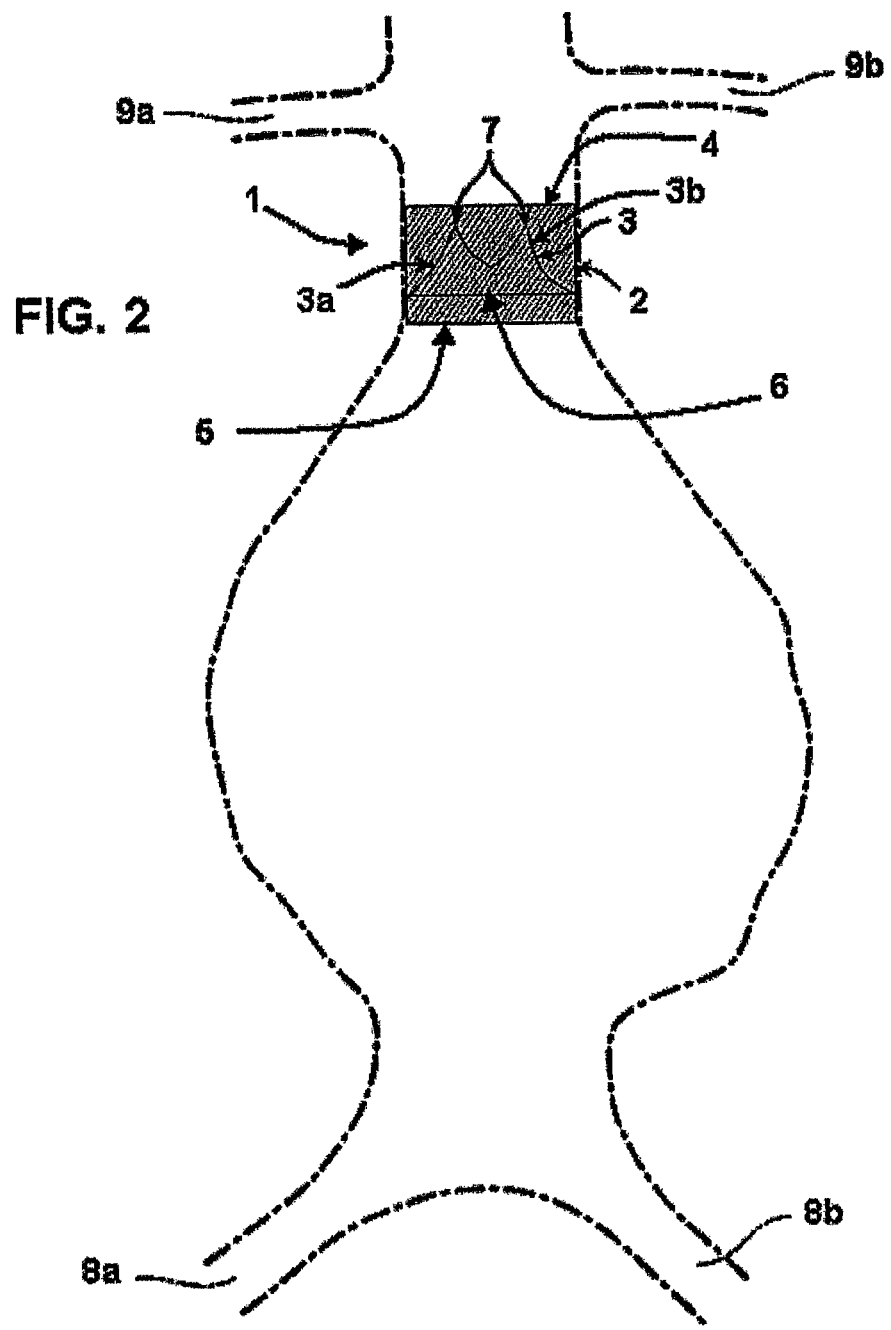
FIG. 2 is a plan view of an endovascular prosthesis of FIG. 1 implanted in abdominal aorta.

One embodiment of the present invention is a prosthesis 1 as shown in FIG. 1-3. The prosthesis 1 is a generally tubular structure which includes a stent 2 and a membrane 3.

The stent 2 of the present invention is similar to those known in the art. The stent 2 can be open-celled or porous which is in direct contact with the aortic wall. This permits ingrowth of cells for the stabilization of implanted endoprosthesis, and device fixation. The stent may further be coated with various materials as known in the art to encourage cell growth therethrough. In addition, the stent 2 may incorporate a covering, or a graft composite (not shown) to prevent blood flow therethrough. The stent 2 may be covered or coated on the stent's exterior, interior or both depending on the application.

As is known in the art, a stent has two diameters, the compressed diameter and the expanded diameter wherein the compressed diameter is substantially smaller than the expanded diameter. The compressed diameter of a stent varies depending on the materials of construction and structure of a stent. In general, the compressed diameter must be small enough to allow for implantation through the vasculature via a minimally invasive deployment system (not shown). The expanded diameter needs to be substantially the same diameter-as the vasculature in which it is to replace or repair. The expanded diameter needs to be large enough to allow a stent to sufficiently secure to the aortic wall without acting as a driving force to expand or dilate the vessel.

Various stent types and stent constructions may be employed in the invention. Stents may be capable of radially contracting, as well, and in this sense can best be described as radially distensible, deformable or conformable. Stents may be balloon expandable or self-expandable. Balloon expanding stents include those that are radially expanded by an applied force. Self-expanding stents include those that have a spring-like action which causes the stent to radially expand, or stents which expand due to the pre-set memory properties of the stent material for a particular configuration at a certain temperature range. Nitinol is one material which has the ability to perform well while both in spring-like elastic mode, as well as in a memory mode based on temperature. Other materials are of course contemplated, such as stainless steel, tantalum, platinum, gold, titanium and other biocompatible metals, as well as shape memory polymers or polymeric based stents, or indeed composites of the aforementioned.

The configuration of a stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding, interlacing or locking of the rings to form a tubular stent structure. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

As shown in FIGS. 1 and 2, stent 2 has a pair of spaced apart ends, a distal end 4, and a proximal end 5, and a tubular wall structure therebetween. The tubular wall structure has an external surface and an internal surface which defines the inner lumen 6 of stent 2. The membrane 3 is supported by stent 2 and extends across the inner lumen 6 of stent 2. The membrane 3 has one or more graft receiving members 7 for sealably receiving at least one tubular graft therethrough. The graft receiving member 7 is defined as a weakened section, a slit, a hole, a penetrable material, a punchout, a puncture, a valve and the like.

Generally, membrane 3 is impermeable to blood, but the membrane material can be permeable to blood and coated to be or become impermeable in situ. Membrane 3 may be made from a variety of well known materials, provided they have the requisite strength characteristics and biocompatibility properties. Membrane 3 is made from a flexible and compressible material. In addition, membrane 3 may be synthetic or natural. Examples of such materials are polymers, elastomers, rubbers, waxes, silicone, parylene, polyurethane, vinyl polycaprolactone, (TEFLON) polytetrafluoroethylene, polypropylene, polyethylene, DACRON, allograph, zenograph material, latex, as well as composites of the aforementioned. Examples of commercially available materials are Corethane (Corvita); Carbothane (Thermedics); Silastic, Pellethane, and Parylene (Specialty Coating Systems). The material can be extruded, knitted, woven, or electrostatically spun material.

Additionally, membrane 3 can be coated or impregnated with bio-erodible, biodegradable or degradable material such as polymers, albumin, collagen, heparin or similar coating material. The membrane could have a coating of a biologically inert material, such as PTFE, or porous polyurethane. The coating can be added to the membrane by methods known in the art such as dipping, spraying or vapor disposition on the material.

The thickness of membrane 3 can vary depending on the application and the material of construction of membrane 3. Generally, the thickness of the membrane is less than the distance between distal end 4 and proximal end 5 of the stent 2. Therefore, some part of stent 2 extends above and/or below membrane 3. For example, in a vascular application membrane 3 can range from 0.001 mm-0.6 mm, preferably 0.1 mm-0.4 mm.

Membrane 3 may be a planar surface or a variety of shapes depending on the application. Membrane 3 can be shaped to assist in bonding membrane 3 to stent 2 and/or to provide sealable securement of a tubular graft to membrane 3. For example, FIG. 1 shows membrane 3 having a peak formation 3a and 3b, having the graft receiving member located at the top of the peak formation 3a and 3b. Thus the top of the peak formation 3a and 3b form one end of the non-planar membrane 3 and the other end of the non-planar is attached to the stent 2. The membrane 3 has a longitudinal length measured from the first end of the membrane 3 to the second end of the membrane. As shown in FIG. 1, the longitudinal length of the membrane 3 is less than the longitudinal length of the stent 2 and the membrane 3 is positioned entirely within the lumen of the stent 2. Also shown in FIG. 1 the peak formation 3a and 3b of the membrane is adjacent to one end of the stent and the other end of the membrane is adjacent the other end of the stent. The peak formation 3a and 3b assist in sealing between a tubular graft and membrane 3 by providing more surface area contact between the two surfaces, shown in FIG. 5 as peak formation 13a and 13b and tubular graft 18. A cup-shape, or sock-shape membrane assists in attaching the membrane within the stent lumen by providing more surface area for the membrane to bond to a stent.

FIGS. 1 and 3 show membrane 3 attached to and supported by inner lumen 6 of the stent 2. Membrane 3 can be attached to stent 2 by adhesive bonding, such as silicone or polyurethane; mechanical attachment, such as sutures or staples; thermal bonding, laminate; or chemical bonding. In addition, the inner surface of stent 2 may be coated with an elastomer or polymer and a solvent may be used to bond the coated inner surface to the membrane. Membrane 3 can be positioned across inner lumen 6 of stent 2 at any location along stent 2 such as across the distal end 4, the proximal end 5 or there between of stent 2.

As shown in FIG. 1-3, the membrane 3 extends transversely across the inner lumen of stent 2 with a peak formation 3a and 3b located centrally in the membrane 3. A graft receiving member 7 is located at the top of each peak formation 3a and 3b. FIG. 2 shows the peak formation 3a and 3b directed in the cephalic direction, but it can be appreciated that the peak formation 3a and 3b can be inverted such that the top of the peak is directed toward the caudal direction, depending on the desired application. In addition to assisting in sealing a tubular graft to the membrane 3, the peak formation 3a and 3b acts as a check valve allowing fluid to flow in one direction across membrane 3, and closes upon no flow of fluid in that direction. Additionally, the peak formation 3a and 3b prevents back flow of fluid in the opposite direction through membrane 3.

Figure 4:
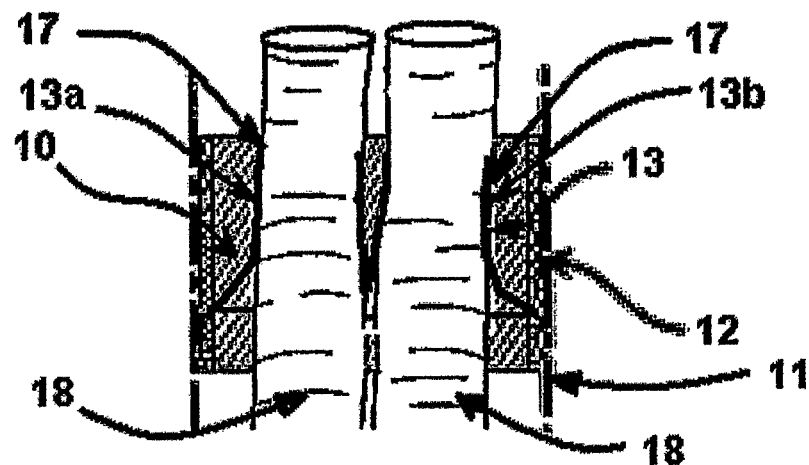
FIG. 4 shows the endovascular prosthesis of FIG. 1 further including grafts.
Figure 5:
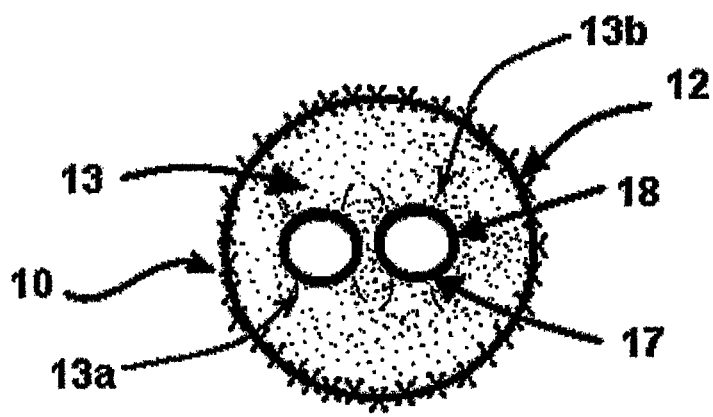
FIG. 5 is a top view of the endovascular prosthesis of FIG. 3 including grafts therethrough.

The prosthesis of the present invention as described above may be used in combination with one or more grafts. As shown in FIGS. 4 and 5, prosthesis 10 is similar to prosthesis 1 of FIG. 1, further including graft 18 extending sealably through graft receiving member 17. The membrane 13 material of the peak formation 13a and 13b conforms around graft 18 and becomes coextensive with a portion of graft 18 securing graft 18 in a sealable manner. Thus the peak formation 13a and 3b of the membrane 13 can be considered a conforming portion. As can be seen in FIG. 4, the inner surface of the peak formation 13a and 13b of the membrane 3 conforms to the outer surface of the graft 18 while the outer surface of the peak formation 13a and 13b of the membrane faces the inner surface of the stent 2. Also as shown in FIG. 4, the majority of the longitudinal length of the membrane 13 conforms to the graft 18. The flow of blood through graft 18 applies outward radial pressure to the graft 18 against membrane 13, more specifically peak formation 13a and 13b. Membrane 13 provides an opposing force against graft 18 provided by the membrane's 13 securement to stent 12 restricting its movement and, additionally, the restricted access of the graft 18 through the graft receiving member 17 of membrane 13. These opposing forces create a seal between graft 18 and membrane 13. It can be appreciated that one or more peaks may be formed in membrane 13 material depending on the application.

As shown in FIG. 4 adjacent to the peak formation 13a and 13b is another portion of the membrane, a second portion, is at an angle relative to the portion of the peak formation 13a and 13b. As shown in FIG. 4, this second portion of the membrane 13 extends from the conforming portion 13a and 13b of the membrane 13 to the stent 2 and has a longitudinal length less than the conforming portion 13a and 13b.

Any known graft material, or tubular prosthesis, and structure may be used to form the graft of the present invention. The graft preferably has generally a tubular configuration. The graft may be made from a variety of well known materials, provided they have the requisite strength characteristics and biocompatibility properties. Examples of such materials are polyester, polypropylene, polyethylene, polytetrafluoroethylene, expanded polytetrafluoroethylene and polyurethane, DACRON, TEFLON (polytetrafluoroethylene), and PTFE coated DACRON as well as composites of the aforementioned. The material can be extruded, woven or knitted, warp or weft knitted. The graft can also be coated or impregnated with a bio-erodible, or degradable material, such as albumin, collagen, heparin or similar coating material. Additionally, the graft could have a coating of a biologically inert material, such as porous polyurethane.

In general, the diameter of graft 18 varies depending on the application but generally at least a portion of graft 18 (or grafts, if multiple grafts used) should be substantially the same diameter as the graft receiving member 17. Generally, the diameter of graft 18 should be large enough to allow for unobstructed blood flow and prevent retrograde pressure build-up in the blood flow while maintaining sufficient traction against membrane 13 for long-term fixation. While cylindrical tubular configurations are shown, other tubular configurations may be employed.

Figure 6:
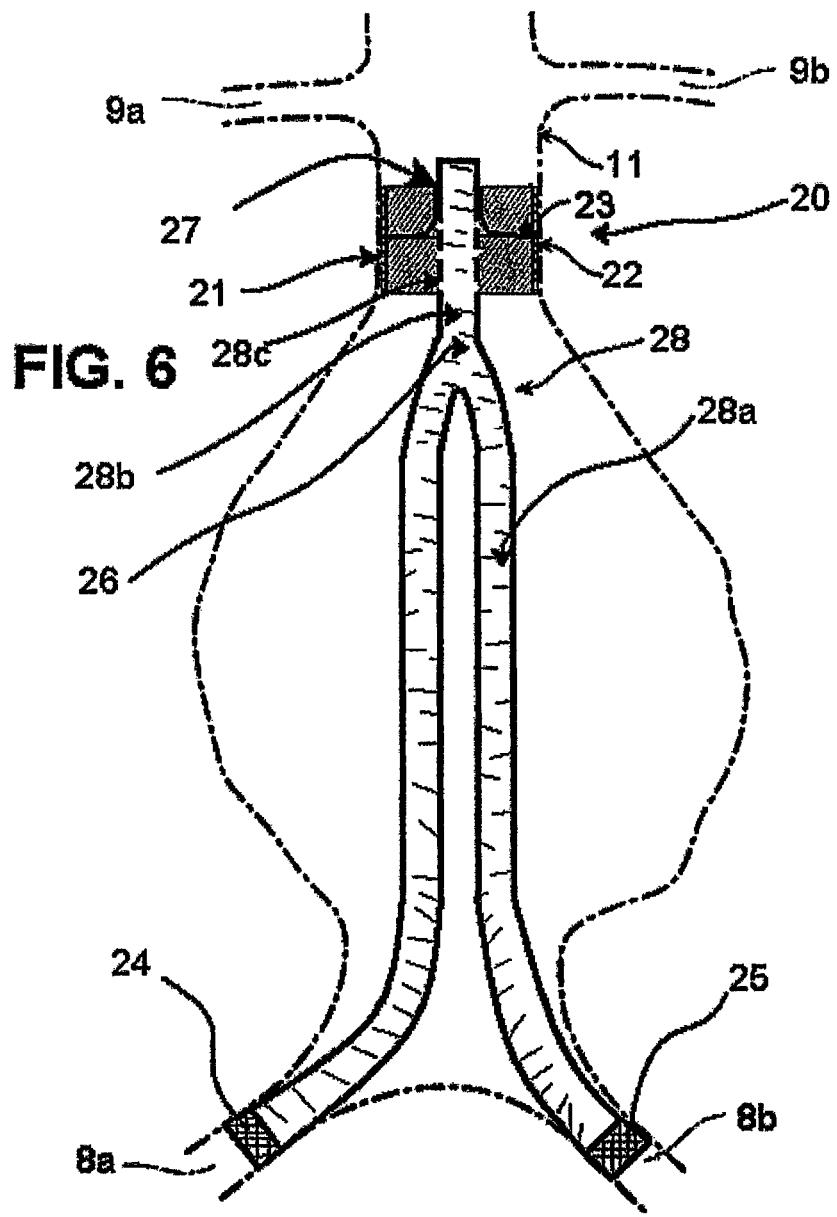
FIG. 6 shows the bifurcated endovascular prosthesis of FIG. 2 including a branched graft.

Another embodiment of the present invention is a bifurcated prosthesis 20 as shown in FIG. 6. FIG. 6 shows a first prosthetic component 21 similar to the prosthesis 1 of FIG. 1 including an expandable stent 22 and a membrane 23 extending transversely across the inner lumen of and attached to the stent 22. Membrane 23 has one or more graft receiving openings 27 or members. The bifurcated prosthesis 20 further includes a second component 26 including a branched graft 28. In one embodiment branched graft 28 has an inverted "Y" shape having two leg portions, 28a and 28b, converging into one trunk portion 28c. The trunk portion 28c extends into graft receiving member 27 of the membrane 17 creating a substantially fluid tight seal between the outer surface of graft 28 and membrane 23. The two leg portions, 28a and 28b, extend into each iliac artery 8 (8a and 8b). The leg portions (28a and 28b) remain in place by the pressure from the blood flowing therethrough and forcing the leg portions (28a and 28b) into each iliac artery 8 (8a and 8b). Additional anchoring stents 24 and 25 can be used in combination with the leg portions (28a and 28b), as shown in FIG. 6, to provide additional securement of graft 17 to the iliac artery wall.

Figure 7:
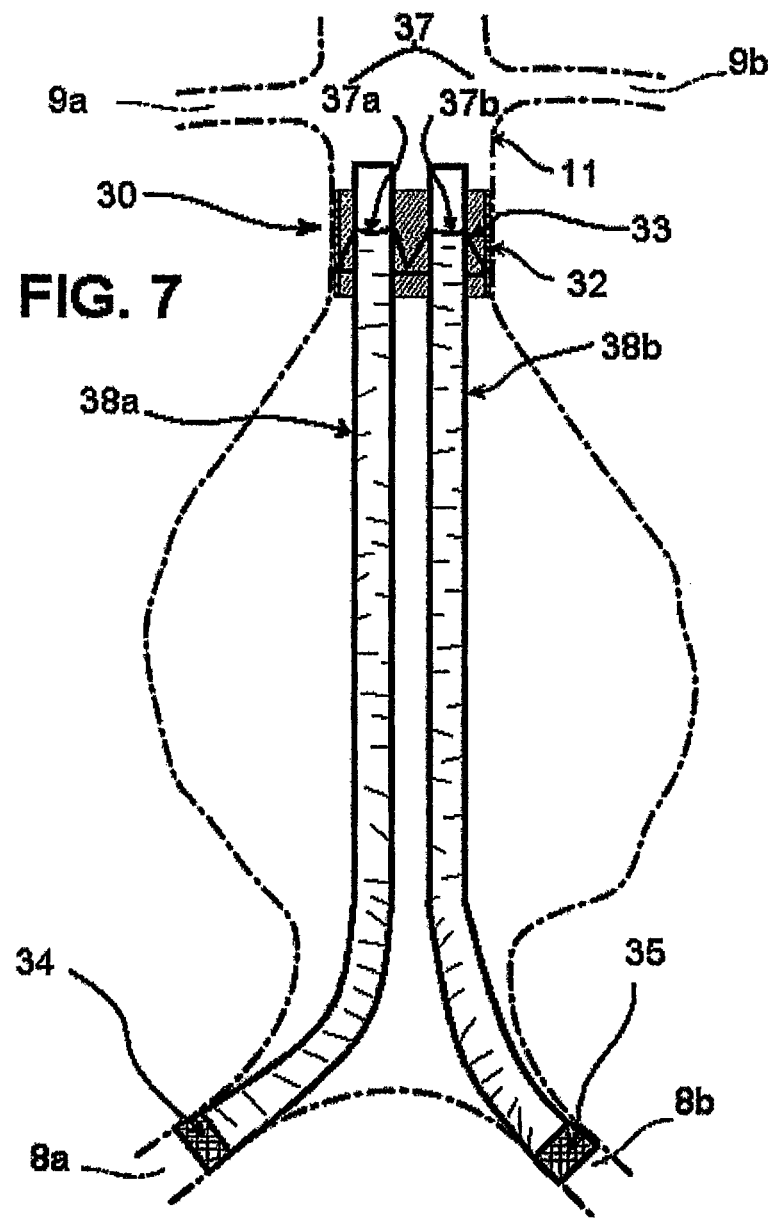
FIG. 7 shows the endovascular prosthesis of FIG. 2 including tubular prosthesis for a bifurcated system.

Another bifurcated embodiment of the present invention is shown in FIG. 7 which is similar to the above described bifurcated prosthesis 20 of FIG. 6 including a stent 32, a membrane 33 extending transversely across the inner lumen of stent 32, graft receiving members 37 and grafts 38. However, the bifurcated prosthesis 30 of FIG. 7 includes two separate graft 38 (38a and 38b) instead of the branched graft 28 of FIG. 6. As shown in FIG. 7, grafts 38 extends into separate graft receiving members 37 (37a and 37b) and form a substantially fluid tight seal between grafts 38 and membrane 33. Additional anchoring stents 34 and 35 can be added for securing grafts 38 to the iliac vessel wall (8a and 8b).

Figure 9:
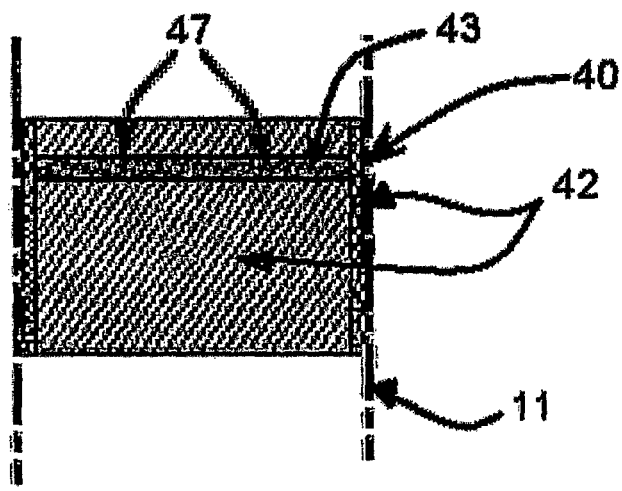
FIG. 9 is a plan view of an endovascular prosthesis of the present invention showing a stent and a membrane.
Figure 10:
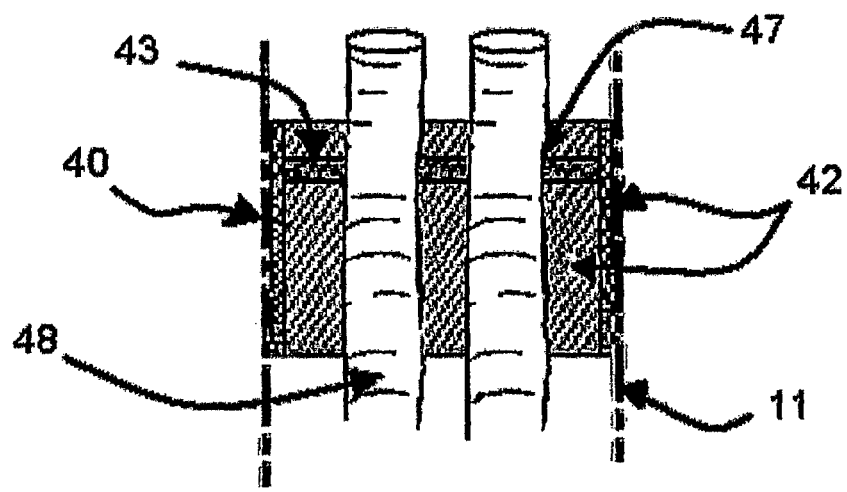
FIG. 10 shows the endovascular prosthesis of FIG. 9 further including tubular graft.

Another embodiment of the present invention is shown in FIGS. 9 and 10 which is similar to the prosthesis 1 of FIG. 1 including an expandable stent 42 and a membrane 43 attached to stent 42 and extending transversely across the lumen of stent 42. Membrane 43 of FIG. 9 includes electrostatically spun material. FIG. 9 shows electrostatically spun material formed into a planar disk shape instead of the peak formation of FIG. 1. The electrostatically spun material has a graft receiving opening 47, similar to graft receiving member 7 of FIG. 1, for sealably receiving at least one tubular graft therethrough. It can be appreciated that a variety membrane 43 of shapes and locations on stent 42 can be used depending on the application, as above-discussed. Generally, electrostatically spun material is similar to material known in the art for vascular grafts. The spun structure of the membrane provides a porous scaffolding structure for blood to clot within and provide a sealable material. The basic process of electrospinning in well known in the art. The process involves the introduction of electrostatic charge to a stream of polymer melt or solution in the presence of a strong electric field. The predominant form of operation entails charge induction in the fluid through contact with a high voltage electrode in a simple metal or glass capillary spinnerette. A charge jet is produced which accelerates and thins in the electric field, ultimately collecting on a grounded device, typically a plate or belt. Under certain conditions of operation, the fluid jet becomes unstable before it reaches the collector. The onset of instability, with low molecular weight fluids, typically results in a spray of small, charged droplets, in a process known as "electrospinning" permitting. Viscoelastic forces stabilize the jet, with polymeric fluids, permitting the formation of small diameter, charged filaments that appear as an "envelope" or a cone dispersed fluid, and that solidify and deposit on the collector in the form of a nonwoven fabric. Under these conditions, it is common to observe mean fiber diameters on the order of 0.1 µm, three orders of magnitude smaller than the diameter of the jet entering the unstable region (10-100 µm). The electrostatic spinning process is described in U.S. Pat. Nos. 4,044,404 and 4,323,525, and is hereby incorporated herein by reference. Additionally, the material is permeable. The pore size of the material will usually be between 0.001µ and 500µ. In order for the material to be sufficiently porous to allow penetration of cells into the surface layers, the average surface pore dimension is preferred to be of the order of 5 to 25µ, more preferably between 7 and 15µ, although pore size in the bulk of the material may average about 1µ. In addition, the membrane may be coated with a material to promote clotting, or provide a non-permeable material to prevent fluid flow, such as collagen, or an elastomer, such as Corethane. Additionally, prosthesis 40 can include multiple layers of materials forming the membrane such as an electrospun layer over a silicon layer.

Prosthesis 40 can be used in combination with various grafts to provide multi-component systems, bifurcated systems, stent-graft prosthesis and the like, as shown in FIG. 10. Prosthesis 40 used in combination with at least one tubular prosthesis 48 extending through the graft receiving opening 47 and sealably supporting the tubular prosthesis 48. Generally, the tubular prosthesis 48 includes a graft which is positioned through graft receiving opening 47 in a compressed state. The graft 48 may vary in size and shape depending on the desired application. For example, a portion of the graft 48 extending on either side of the graft receiving opening 47 may have a larger diameter opening than the portion extending through the graft receiving opening 47 to provide for additional securement of the graft 48 to the membrane 43. Once in place, the graft 48 is allowed to expand in the graft receiving opening 47. The pressure from the blood through the graft 48 secures the graft 48 to the electrostatically spun membrane, as similar described above in regards to prosthesis 1 of FIG. 1.

The above described prosthesis as shown in FIGS. 1-10 can be loaded into a delivery system for deployment within, a body lumen. The delivery system used is similar to those known in the art. Typically, the delivery system has an introductory device or sheath in which the prosthesis is compressed therein. Once the desired vascular site is reached, the sheath is removed, leaving the stent and attached membrane located endoluminally. Additional components may be used in combination with the above deployed prosthesis such as a tubular graft. A tubular graft is deployed after the initial prosthesis is deployed using the same delivery device with an additional sheath or a separate device.

Generally, in regards to prosthesis 1 of FIG. 1, the delivery system includes an elongated outer sheath which supports the prosthesis 1 in a compressed condition. The outer sheath is an elongated generally tubular structure which longitudinally surrounds the prosthesis 1. The outer sheath has a diameter which is sufficiently small so as to be readily inserted within a body lumen.

The deployment system may further include guidewires, multiple sheaths, dilation devices, i.e. balloons, nose caps and pushers, as known in the art.

When the delivery system is positioned at the desired site in the body lumen the outer sheath is retracted with respect to the prosthesis 1. The retraction of the outer sheath progressively releases stent 2 along its longitudinal (axial) extent and allows the stent 2 to radially expand. As stent 2 further expands membrane 3, which is positioned within the stent 2, is deployed. Membrane 3 radially deploys by the radially expanding force of attached stent 2.

Prosthesis 40 as shown in FIG. 9 may be deployed using the same method as described above, and known in the art.

Deploying the above-described prosthesis in combination with a graft is a multi-step deployment process. The initial step is deploying the first prosthesis including the stent and attached membrane as above-described.

Generally, after the first prosthesis is positioned and deployed then the tubular prosthesis is positioned and deployed using various systems as known in the art. For example, additional sheaths may be added to the first delivery device, above-described, to deploy the tubular graft after deploying the first prosthesis. An example of a multi-stage delivery device which is useful for delivering the first prosthesis and tubular prosthesis is described in U.S. Pat. No. 6,123,723 to Konya, and is hereby incorporated herein by reference. Alternatively, second separate delivery system can be used to deploy the tubular prosthesis. After the initial prosthesis is deployed as described above, an additional deployment device is used to position the tubular prosthesis within the graft receiving member of the membrane. Once the additional deployment device is in position the sheath is retracted allowing the tubular prosthesis to be placed within the graft receiving member. The tubular prosthesis securably seals to the membrane by the blood flowing through the tubular prosthesis and forcing the tubular prosthesis to radially expand against the membrane. Additionally, stents may be deployed to secure the tubular prosthesis to the arteries.

Figure 8:
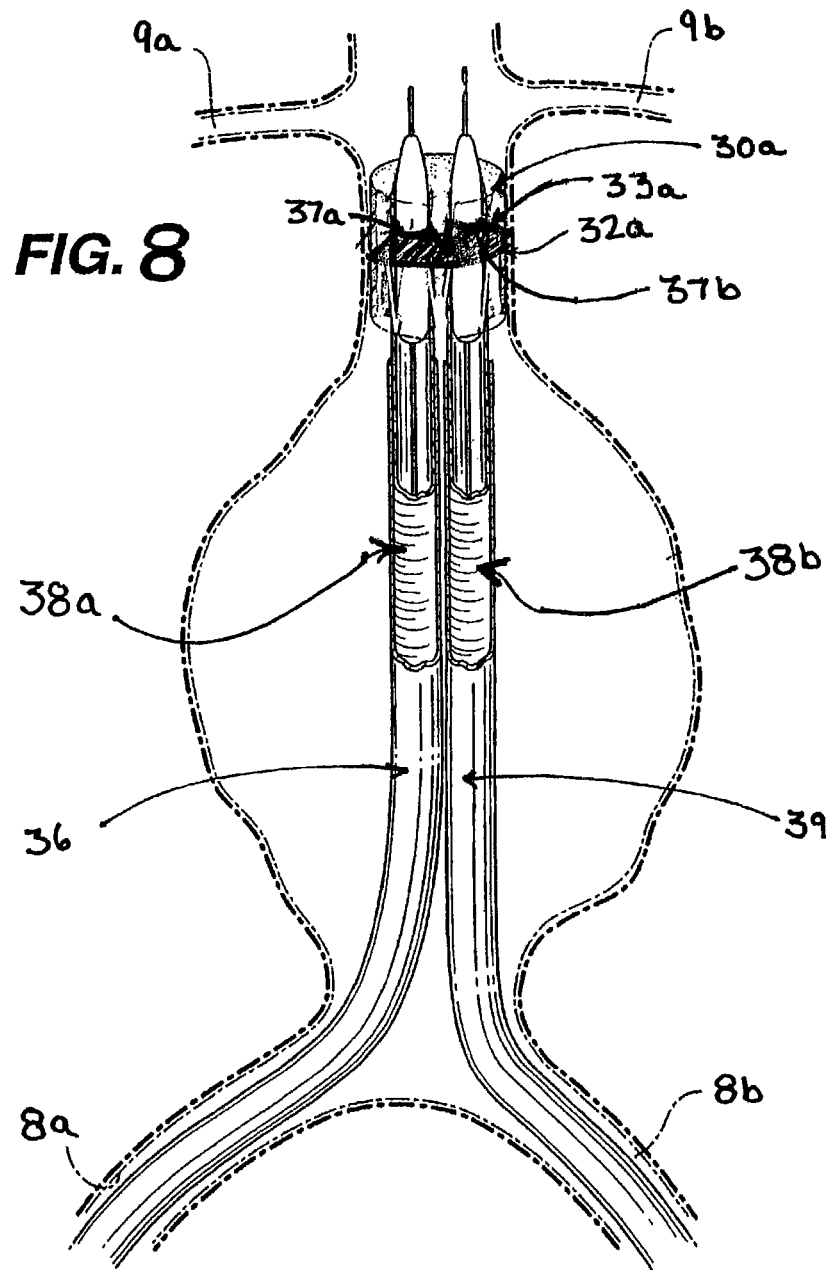
FIG. 8 shows the endovascular prosthesis of FIG. 7 showing a deployment of tubular prosthesis for a bifurcated system.

Similarly, a bifurcated system uses the same multi-step delivery process, as above-described. Additional sheaths and/or deployment devices are used to deploy the tubular prosthesis as above-described. For example, FIG. 8 shows a bifurcated system where the tubular prosthesis are being implanted after the initial prosthesis 30a including stent 32a and attached membrane 33a is deployed. The tubular prosthesis 38a and 38b are navigated to the abdomen. This would be accomplished by mounting the tubular prosthesis 38a and 38b onto catheters 36 and 39 and thereafter percutaneously inserting the catheters into a femoral artery and navigating the tubular prosthesis to the target site. Guidewires can be used to help delivery of the catheter to the target site. Navigating catheters within the human arterial system is well known in the art. An example of a balloon catheter is given in U.S. Pat. No. 5,304,197 issued to Pinchuck et al. on Apr. 19, 1994, which is hereby incorporated herein by reference. The target site is, as previously mentioned, through the graft receiving member 37a and 37b of the membrane 33a. The sheath of the catheter is removed, placing the tubular prosthesis 38a and 38b within the graft receiving members 37a and 37b. Removal of the catheter permits the blood to flow through the tubular prosthesis 38a and 38b further securing such prosthesis 38a and 38b within the graft receiving members 37a and 37b, and ultimately sealably securing the tubular prosthesis 38a and 38b to the stent 32a. Distal anchoring stents (not shown) can be used to secure the tubular prosthesis 38a and 38b to the walls of the iliac arteries. Distal anchoring stents can be mounted on and deployed using the same catheter as used delivering the tubular prosthesis 38a and 38b. Alternatively, the anchoring stents can be deployed by using a separate deployment device after placement of the tubular prosthesis 38a and 38b has been completed.

FIG. 7 shows how the entire system looks after the bifurcated prosthesis 30 including stent 32 and attached membrane 33, grafts 38 and anchoring stents 34 and 35 have been deployed.

The delivery of prosthesis 20 including a branched graft 28 of FIG. 6 is similar to the delivery of prosthesis 30 of FIG. 8.

Initially the prosthesis 20 including stent 22 and attached membrane 23 are delivered to the desired sight as above-described. A second delivery system is used to implant the branched graft 28 in a compressed state within the graft receiving member 27 of the membrane 23. Once in place the sheath is removed allowing graft 28 to expand within the graft receiving member 27, one leg 28a of graft 28 is in place and may be anchored with an anchoring stent 24. A third delivery device is used to properly position the other leg 28b of the branched graft 28 and additionally add an anchoring stent 25 to secure the graft within the iliac artery 8b. FIG. 6 shows how the entire system looks after the prosthesis 20 including the branched graft 28 is deployed.

Figure 11:
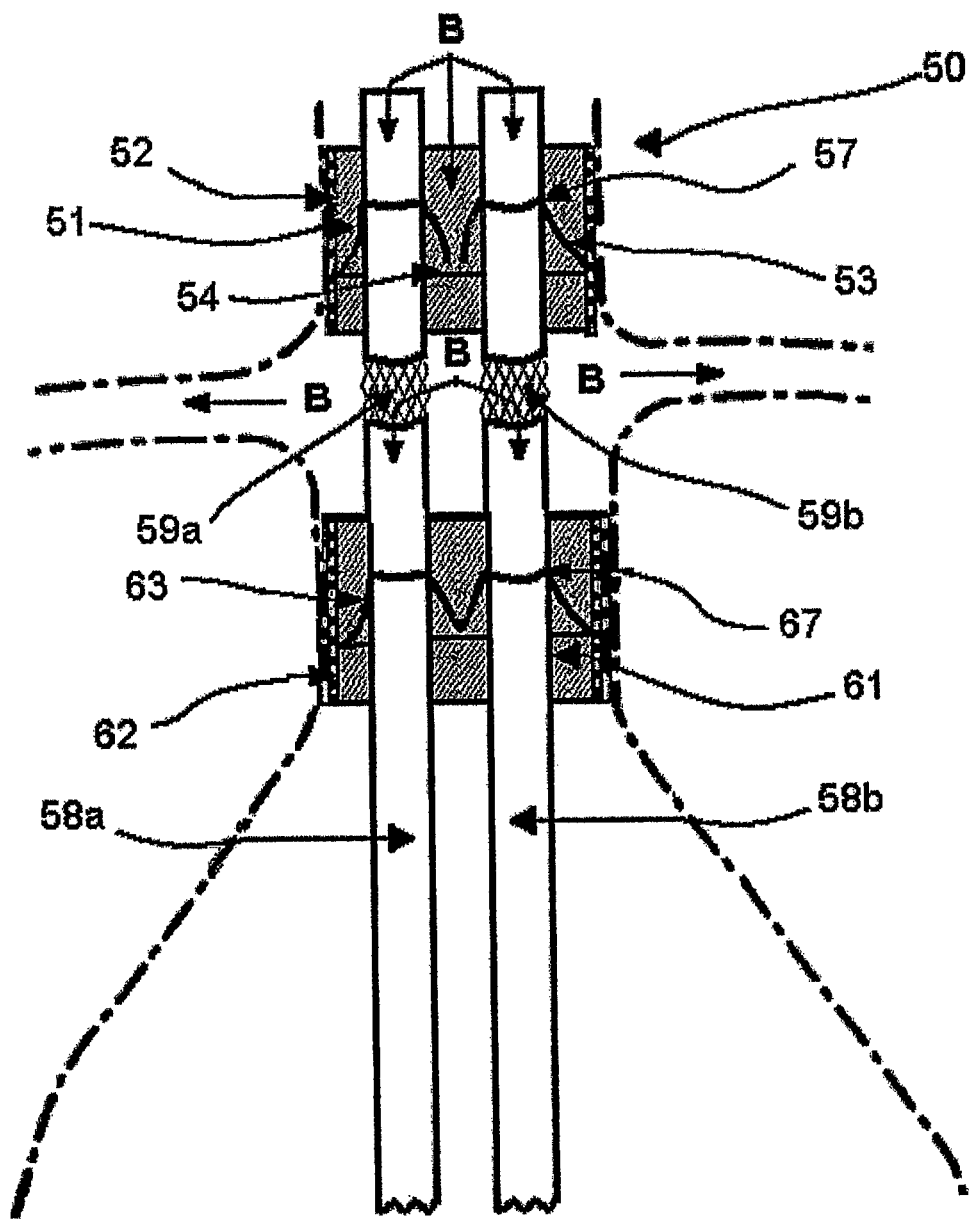
FIG. 11 shows a multi-component endovascular prosthetic system of the present invention.

It may be desirable to have additional securement of the prosthesis to the aortic wall. Multiple prosthesis, as described above, can be used in combination to offer securement of the prosthesis cephalically to the renal arteries. For example, FIG. 11 shows a multi-component endovascular prosthesis 50 of the present invention which includes a first expandable prosthesis 51, and second expandable prosthesis 61. The prosthesis, 51 and 61, are similar to the prosthesis 1 in FIG. 1 including a stent, and a membrane extending traversely across the inner lumen and attached to the stent, and having one or more graft receiving members. The first expandable prosthesis 51 and second expandable prosthesis 61 include an expandable stent (52, 62), and a membrane (53, 63) having graft receiving openings (57, 67), respectively. FIG. 11 shows the first expandable prosthesis 51 further including fluid flow opening 54 to provide an outlet for fluid to flow through the membrane 53. The fluid flow opening 54 includes a slit, a hole, a fluid penetrable material and the like. FIG. 11 shows a bifurcated system including tubular grafts 58 (which includes 58a and 58b) which extends sealably through each prosthesis, (51, 61) at the graft receiving opening (57, 67) for directing fluid through the tubular grafts 58. In addition, FIG. 11 shows grafts 58 including a porous portion 59 (which includes 59a and 59b) disposed on grafts 58 between the first expandable prosthesis 51 and the second expandable prosthesis 61 to allow for fluid exchange through the porous portion 59 of grafts 58. The porous portion 59 includes a stent, slits, fluid permeable material and the like.

Deployment of prosthesis 50 is similar to those prosthesis as above-described. For an abdominal aortic aneurysm application, the first expandable prosthesis 51 is positioned and deployed cephalic to the renal arteries 9 (includes 9a and 9b) via a delivery device in the same manner as described above. The same delivery device using additional sheaths or a second delivery device is used to implant second expandable prosthesis 61 between the renal arteries 9 and the abdominal aneurysm. An additional delivery device is used to deliver grafts 58 through the graft receiving opening (57, 67). Graft 58a is extended through graft receiving opening (57, 67) of each prosthesis (51, 61), respectively. Second graft 58b is extended through graft receiving opening (57, 67). Grafts 58a and 58b are extended sealable through the graft receiving openings (57,67) for directing fluid therethrough. The same deployment procedure as above-discussed is used to delivery prosthesis 50, as known in the art.

Figure 12:
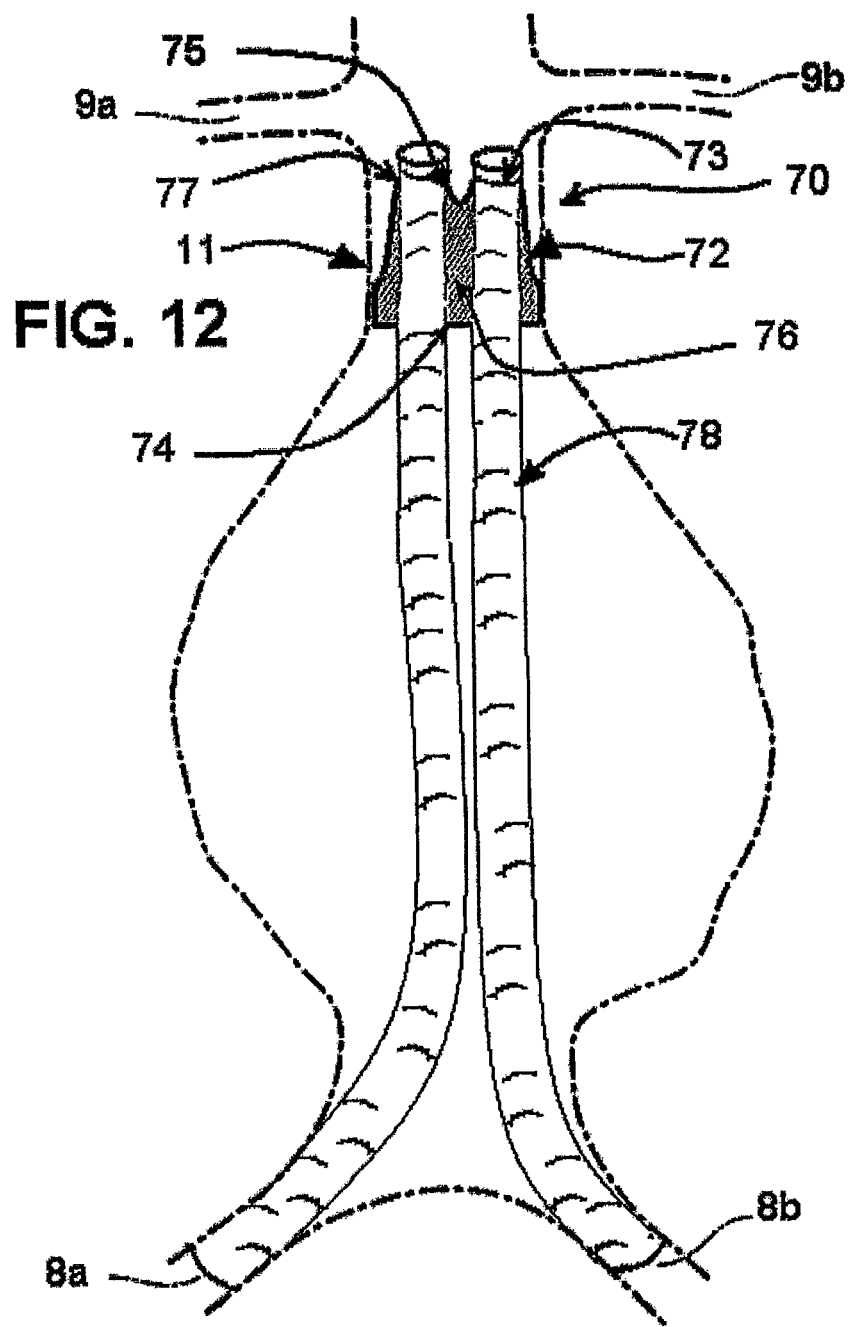
FIG. 12 shows an endovascular prosthesis of the present invention combined with tubular grafts.
Figure 13:
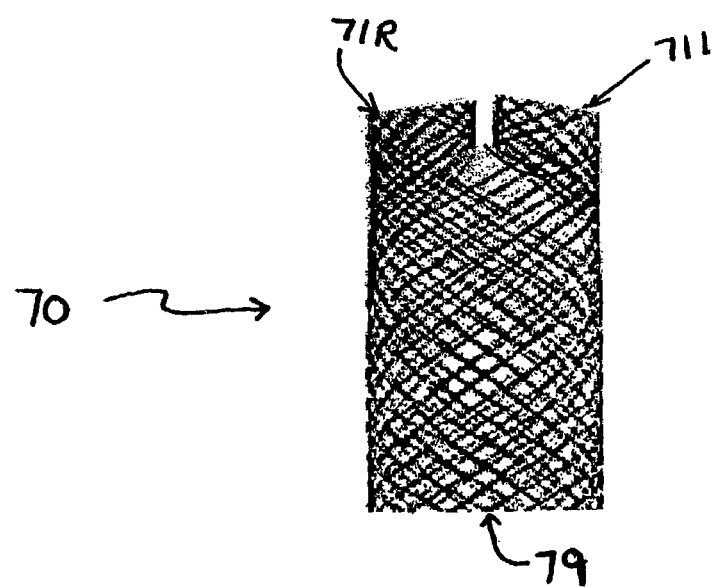
FIG. 13 is an enlarged plan view of an endovascular prosthesis of FIG. 12 including a stent and attached membrane.

A further embodiment of the present invention is an endovascular prosthesis 70 of FIG. 12, which is similar to prosthesis 1, of FIG. 1 including a stent and a membrane. FIG. 12 shows the "M" shaped stent 72 having an inner lumen 76, a distal end 74 and a proximal end 75. The distal end 74 has an opening and the proximal end 75 has two openings opposed the distal opening. A puncturable membrane 73 extends across each of the proximal end 75 openings for puncturably receiving a graft. The stent 72 of FIG. 12 is similar to the stents as above-described but is preferably a weave or braid of stent filaments. As shown in FIG. 13, a typical braided stent includes a first set of filaments 71L wound in a first helical direction (to the left as shown in FIG. 13) and a second set of filaments 71R wound in a second, opposite helical direction (to the right as shown in FIG. 13), forming a plurality of overlaps 79. Filaments 71L and 71R may be wire, such as nitinol or stainless steel, or may comprise polymer or any type of filaments known in the art. The prosthesis 70 may be a hybrid material having two materials woven or bonded together such as a PTFE and Dacron, where Dacron is bonded on the exterior of the PTFE.

As used herein, a "braided" stent refers to a stent formed of at least two continuous filaments which are interwoven in a pattern, thus forming overlaps 79 as shown in FIG. 13. At each overlap, one filament is positioned radially outward relative to the other filament. Following each filament along its helical path through a series of consecutive overlaps, that filament may, for example be in the radial inward position in one overlap and in the radial outward position in a next overlap, or may in the inward position for two overlaps and in the outward position for the next two, and so on. Exemplary braided stents are disclosed in U.S. Pat. No. 4,655,771 to Hans I. Wallsten, and is incorporated herein by referred. The endovascular prosthesis 70 may include a stent-graft composite where the stent is an open structure with a non-permeable graft material attached thereto. A stent-graft composite can further have a stent with one opening at the distal end and a crimped opening at the proximal end supporting a graft which forms the two openings at the proximal end 75.

The endovascular prosthesis of FIG. 12 further includes a puncturable membrane 73 which is similar to membrane 3 of FIG. 1 as described-above having weakened section, opening, slit, or hole for receiving a graft therethrough. Membrane 73 is similarly attached to stent 72 as described above by mechanical, thermal, chemical, and adhesively attached. Membrane 73 and/or graft receiving opening 77 forms a fluid seal between the tubular prosthesis 78 and the stent 72 at the proximal end 75.

The endovascular prosthesis 70 of FIG. 12 is shown in combination with tubular prosthesis 78. Any number of tubular grafts may be used depending on the application. FIG. 12 shows the tubular prosthesis 78 extending through the distal end 74 opening of the prosthesis 70 and puncturably through membrane 73 thereby forming a fluid seal between the tubular prosthesis 78 and the stent 72 at the proximal end 75. Blood flow is directed through the tubular prosthesis 78. The tubular prosthesis 78 are positioned in each iliac artery so that the blood exits the tubular prosthesis 78 into each iliac artery (8a, 8b).

The deployment of prosthesis 70 is similar to the manner of deployment described for prosthesis 1 of FIG. 1. Generally, the delivery system is positioned in the body lumen, and the outer sheath is retracted with respect to the prosthesis 70. The retraction of the outer sheath progressively releases the stent 72 along its longitudinal (axial) extent and allows the stent 72 to radially expand. The membrane 73, which is positioned across the stent lumen 76, is radially deployed by the radially expanding force of the attached stent 72.

Additionally, secondary delivery devices are used to deploy tubular prosthesis 78 through the graft receiving membrane 77, similar to those above-described. The implanted bifurcated system is shown in FIG. 12.

Figure 14:
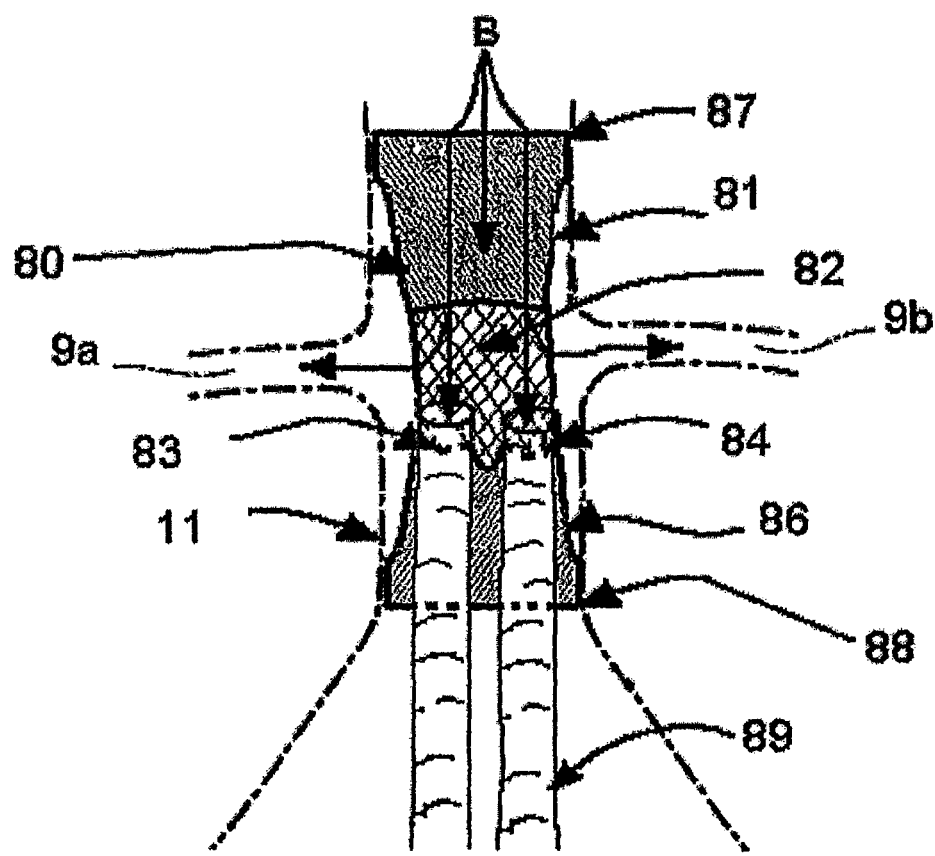
FIG. 14 is a plan view of an endovascular prosthesis of the present invention showing a stent, grafts and membranes in combination with tubular grafts.

A further embodiment of the present invention similar to FIG. 12 is shown in FIG. 14 which provides for additional securement of the prosthesis cephalically to the renal arteries 9 (includes 9a and 9b). FIG. 14 shows an endovascular prosthesis 80 where a portion of the prosthesis 80 caudal to the renal arteries 9, similar to the embodiment 70 of FIG. 12, has an "M" shaped configuration with an opening at one end and two openings 84 at the opposed end. The endovascular prosthesis 80 of FIG. 14 is a graft-stent composite including a stent 82, grafts 86 and membranes 83. The stent 82 extends the full length of the prosthesis 80 having a distal end 87, a proximal end 88 and an opening extending therethrough. As shown in FIG. 14, a portion of the endovascular prosthesis 80 cephalic to the renal arteries 9 includes a first graft 81 which is attached to the distal end 87 of the stent 82 having an inner lumen therethrough. A portion of the prosthesis 80 caudal to the renal arteries 9 includes a second graft 86 which is attached to the proximal end 88 of the stent 82 and forms the "M" shape, similar to the prosthesis 80 of FIG. 14. The second graft 86 forms two smaller lumens 84 within the stent 82 opening. Membrane 83 extends transversely across each of the two lumens 84 of the second graft 86. Membrane 83 is similar to the construction materials as described for that of prosthesis 1 of FIG. 1. Membrane 83 can be attached to graft 86, in the manner as above-described, by adhesive bonding, such as silicone or polyurethane; mechanical attachment, such as sutures or staples; thermal bonding, laminate; or chemical bonding. The two grafts 81 and 86 are spaced apart to provide for blood exchange through the stent 82 and renal arteries 9. The section of the stent 82 between the first graft 81 and second graft 86 may be an open celled structure or a covered stent which is blood-permeable. FIG. 14 shows the endovascular prosthesis 80 having a wider cross-sectional area at distal end 87 and proximal end 88 where the stent 82 secures the prosthesis 80 to the artery wall, and a narrow cross-sectional area there between. One can appreciate that the endovascular prosthesis 80 may be one cross-sectional area throughout the length of the prosthesis 80 or varying cross-sectional areas as long as the two ends provide for securement to the artery wall and allow for undisturbed blood-flow therethrough.

Prosthesis 80 can be used in combination with a tubular prosthesis 89 as shown in FIG. 14. The tubular prosthesis 89 extends through each of the respective membranes 83 and provides a sealable attachment between the graft 86 and the tubular prosthesis 89. The blood is diverted into each tubular prosthesis 89. The tubular prosthesis 89 is those known in the art and above-described in reference to the prosthesis 10 in FIG. 4.

To deploy the prosthesis 80, the prosthesis 80 is typically compressed into a radially compressed state into a delivery device, as known in the art and above-described. The prosthesis 80 is then introduced to the lumen into which it is to be deployed, navigated through the lumen to a deployment location, typically a diseased artery such as the aorta. The prosthesis 80 is expanded to a radially expanded state in the deployment location as is known in the art. FIG. 14 shows the prosthesis 80 deployed across the renal arties 9a and 9b where the open-cell structure or porous portion of the prosthesis 80 is between the renal arteries 9a and 9b. The deployment of the tubular prosthesis 89 (89a and 89b) of the present invention is thus deployed by a method similar to that described above using a separate delivery device or the same delivery device with additional sheaths or stages, as known in the art. The tubular prosthesis 89 are puncturably delivered through the membrane 83. The tubular prosthesis are sealably secured to the graft 86 by the outward force from the blood flowing there through and the restricted size of the lumens 84.

Figure 15:
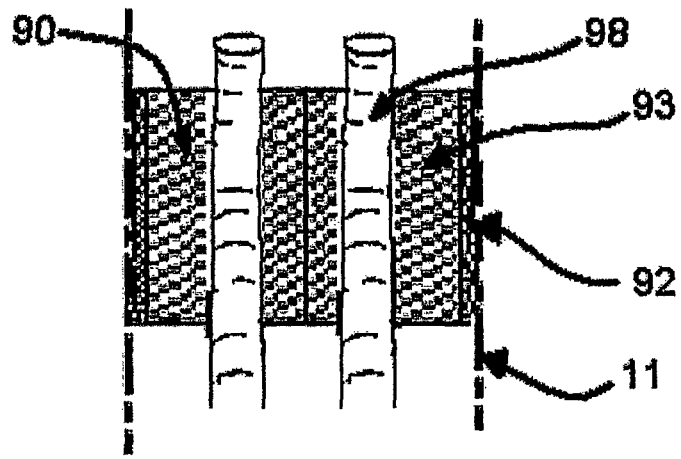
FIG. 15 is a plan view of the endovascular prosthesis system of the present invention showing the expandable foam in the expanded state.
Figure 16:
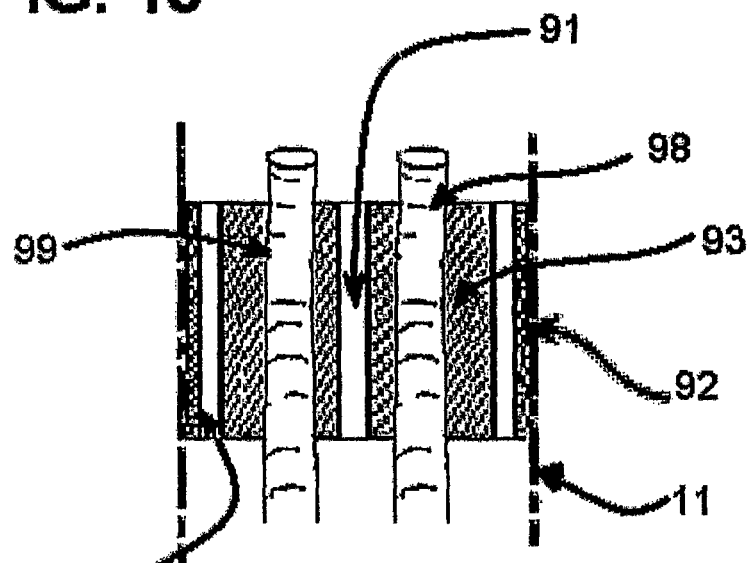
FIG. 16 shows the endovascular prosthetic assembly of FIG. 15 showing the expandable foam.

Another embodiment of the present invention which is similar to prosthesis 1 of FIG. 1 but instead of using a membrane to sealable secure a tubular prosthesis to the stent, a foam 93 is used to securely attaching the tubular prosthesis 98 to the stent 92 as shown in FIG. 15. The endoprosthesis 90 of FIG. 15 includes a stent 92, and a tubular prosthesis 98 having an expanded foam 93 attached thereto. The stent 92 is similar to those described above being an expandable stent 92 having a distal end, a proximal end and an inner lumen. As shown in FIG. 16, stent 92 has an inner surface 94 and an outer surface. The tubular prosthesis 98 is similar to those described above having an interior surface and exterior surface 99. The expanded foam 93 is attached to the exterior surface 99 of the tubular prosthesis 98. The tubular prosthesis 98 is placed within the lumen 91 of the stent 92 and the expanded foam 93 sealably secures the tubular prosthesis 98 to the stent 92.

The expandable foam 93 must be biocompatible and requisite strength characteristics. The foam is similar to those known in the art such as gelatin sponge, collagen sponge, cellulose sponge, hyaluronic acid and foams used for nasal surgery. The expandable foam 93 may be porous or non-porous. The expandable foam 93 is provided in a compressed state prior to placement within the stent 92. Once in place, the expandable foam 93 is allowed to expand into the matrix of stent 92 to securably attach the tubular prosthesis 98 in the stent lumen 91. Some expandable foams are non-permeable upon implantation, while others provide a scaffold structure for clot formation. Some scaffold structure foams may dissolve over time leaving a sealable clot formation. Suitable available commercial foams include Spongostern, Surgifoam, (Ferrosan, distributed by Johnson & Johnson); Gelfoam (Pharmacia & UpJohn Company); Avitene Ultrofoam (Bard/Davol); MeroGel Nasal Dressing, Sinus Stent and Otologic Packing, HYAFF (Medtronic Xomed, Jacksonville, Fla.).

The expandable foam 93 is attached to the outer surface 99 of the tubular prosthesis 98 by mechanical, adhesive, thermal, or chemical attachment. As shown in FIG. 16, the foam 93 covered graft 98 is placed into the lumen 91 of the stent 92 and the expandable foam 93 is allowed to expand by either a reaction in the vascular environment, such as hydrolysis, or by removing an outside force, such as sheath. The expandable foam 93 expands against and into the structure of the stent 92 securing the tubular prosthesis 98 in place in a sealable manner. A s shown in FIG. 16 one or more tubular prosthesis 98 can be used depending on the application.

Figure 17:
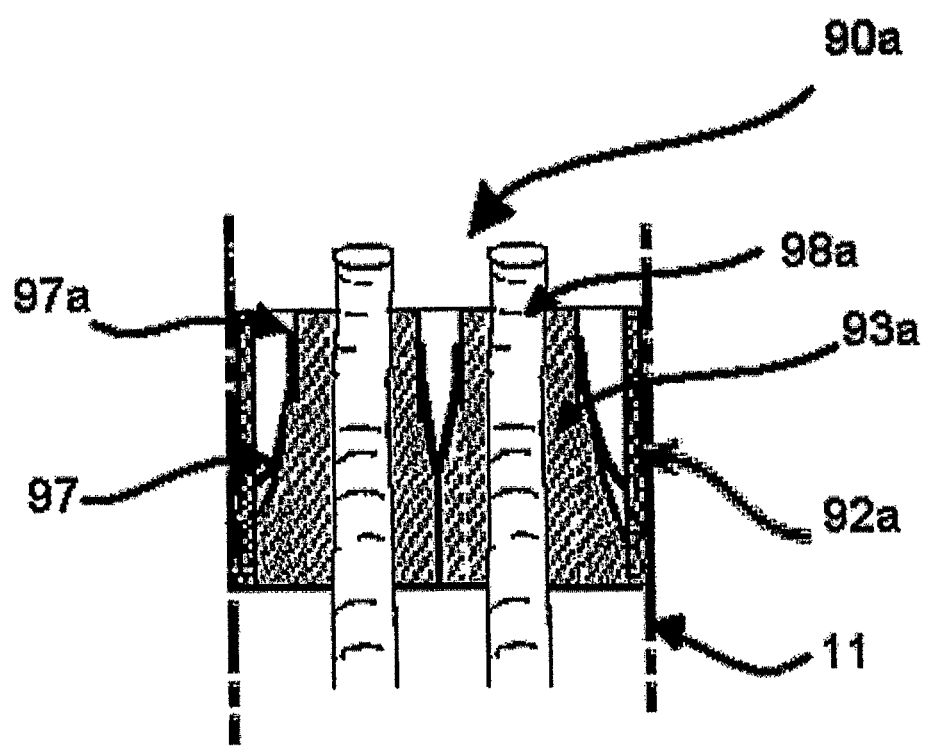
FIG. 17 is a plan view of an endovascular prosthesis of the present invention showing a stent having an attached membrane in combination with an expandable foam.

Additionally, as shown in FIG. 17, the expandable foam 93 covered tubular prosthesis 98 of FIG. 16 can be used in combination with the prosthesis 1 of FIG. 1. Prosthesis 90a includes a stent 92a and a membrane 97 having a graft receiving member 97a, similar to prosthesis 1 of FIG. 1. The expandable foam 93a covered tubular prosthesis 98a is extended through the graft receiving member 97a. The expandable foam 93a expands within the graft receiving member 97a to provide a sealable securement of the tubular prosthesis 98a to the membrane 97, as shown in FIG. 17.

Further the embodiment of the present invention is a kit of parts for assembly into an endovascular prosthetic system. The kit includes an expandable stent 92 and a tubular prosthesis 98. The expandable stent 92 has a distal end, a proximal end and an inner lumen 91 for insertion into a body endovascularly. The tubular prosthesis 98 is adapted to be inserted within the inner lumen 91 of the stent 92. The tubular prosthesis 98 has an interior surface for body fluid flow and an exterior surface. Additionally, an expandable foam 93 is attached to the exterior surface of the tubular prosthesis 98. The expandable foam 93 is adapted to expand within the stent 92 to sealably secure the tubular prosthesis 98 to the stent 92.

Deploying prosthesis 90 is similar to the method of deploying prosthesis 30 of FIG. 7. The prosthesis 90 is a multi-step process as above-discussed. The stent 92 is typically compressed into a radially compressed state into a delivery device, as known in the art. The stent 92 is then introduced into the lumen in which it is to be deployed, navigated through the lumen to a deployment location, and then expanded to a radially expanded state in the deployment location, as is known in the art. The expandable foam 93 covered tubular prosthesis 98 are also compressed into a radially compressed state into a delivery device. Once the tubular prosthesis 98 are positioned within the stent lumen 91 the tubular prosthesis 98 are deployed by removing a restraining element, such as a sheath, of the delivery device. The expandable foam 93 is allowed to expand filling the space within the stent lumen 91, into the structure of the stent 92, and sealably securing the tubular prosthesis 98 within the stent 92. As above-discussed separate delivery devices may be used to deploy each component of the prosthesis 90 or a multi-step delivery device may be used.

In addition, prosthesis 90a of FIG. 17 is deployed using the same delivery system as above-described for prosthesis 90 of FIG. 16, except the stent 92 of FIG. 16 is substituted with the first prosthesis 91a. Initially, first prosthesis 91a is compressed in a delivery device, delivered to the target site within the lumen and allowed to deploy at the site. The expandable foam 93a covered tubular prosthesis 98a are delivered via the delivery device in a compressed state into the graft receiving member 97a. After placing the delivery device within the graft receiving members 97a at the desired location, the delivery device is removed to allow the expandable foam 93a to expand within the graft receiving members 97a. The expandable foam 93a in combination with the graft receiving members 97a sealably secure the tubular prosthesis 98a to the first prosthesis 91a.

Figure 18:
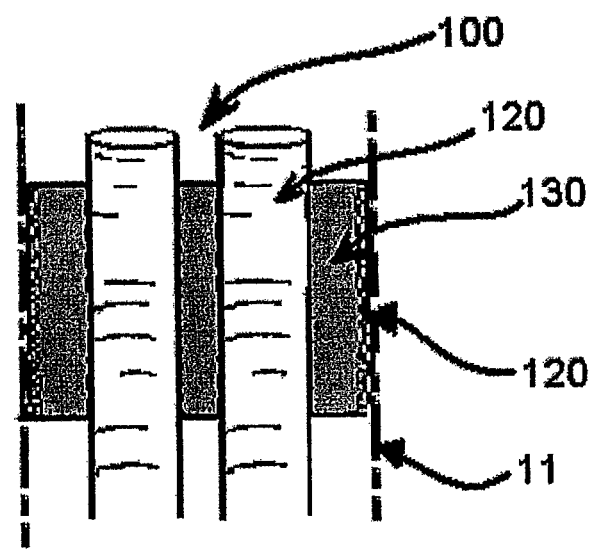
FIG. 18 is a plan view of an endovascular prosthetic system of the present invention showing a polymeric material sealably supporting a tubular graft to a stent.
Figure 19:
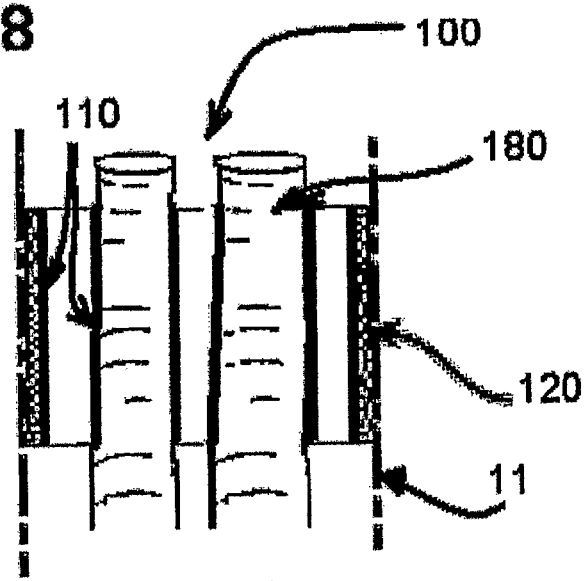
FIG. 19 shows the endovascular prosthetic system of FIG. 18 showing a primary reactive material on a graft and stent.

A further embodiment of the present invention is an endovascular prosthetic assembly 100 as shown in FIGS. 18 and 19 which is similar to the prosthesis 90 of FIG. 15 but instead of using an expandable foam on the grafts to secure the grafts to the stent, a polymeric material 130 is used. FIG. 19 shows the endovascular prosthetic assembly 100 including a stent 120 and a tubular prosthesis 180 similar to those described above. Endovascular prosthetic assembly 100 further includes a polymeric material 130 sealably supporting the tubular prosthesis 180 to the stent 120. The polymeric material 130 is a substantially homogenous reaction product of monomer materials which is formed in situ. As shown in FIG. 18, the exterior surface of the tubular prosthesis 180 and inner surface of the lumen of the stent 120 are pre-coated with a primary reactive material 110. The tubular prosthesis 180 is positioned within the inner lumen of the stent 120. A secondary material (not shown) reactive with the primary material 110 is introduced in the vicinity of tubular prosthesis 180 and the inner lumen of the stent 120. The primary material 110 and secondary material react forming a polymeric material 130 which sealably supports the tubular prosthesis 180 to the stent 120.

In general, the polymeric material 130 is biocompatible, slightly thrombotic, and non-toxic. The polymeric material 130 can be a foam or hydrogel. A hydrogel which is useful is one formed from the mixture of a polymer and monomer and an reaction promoter such as a chemical activator or light activator (focal therapeutic). Examples of suitable materials which react to form a hydrogel include polyethylene glycol and iron, or polyethylene glycol and peroxide in addition to light activation or a chemical activator. For additional suitable hydrogel and methods of preparation, refer to U.S. Pat. No. 6,379,373 to Sawhney, which is hereby incorporated herein by reference.

In addition, one or more tubular prosthesis 180 can be used depending on the application. The prosthesis 100 can be offered in a kit form. The kit of parts for assembly into an endovascular prosthetic system 100 includes a stent 120, a primary reactive material 110, a tubular prosthesis 180, and a secondary reactive material. The stent 120 has an inner surface, an outer surface and an inner lumen. The primary reactive material 110 is disposed on said inner surface of the stent 120. The tubular prosthesis 180 is adapted to extend within the inner lumen of the stent 120. The tubular prosthesis 180 has an interior surface and an exterior surface, and the primary material 110 is disposed on said exterior surface of the tubular prosthesis 180. The secondary material is reactive with the primary material 110 and adapted to be applied to the primary material 110 upon insertion of the tubular prosthesis 180 within the inner lumen of the stent 180. The secondary material is reactive with the primary material 110 to form a seal between the tubular prosthesis 180 and the stent 120.

Deploying prosthesis 100 is similar to the deployment process of prosthesis 90 of FIG. 15. The prosthesis 100 is also a multiple step process as above-discussed. The stent 120 is compressed into a radially compressed state into a delivery device, as known in the art. The stent 120 is then introduced to the lumen into which it is to be deployed, navigated through the lumen to a deployment location, and then expanded to a radially expanded state in the deployment location, as is known in the art. Secondarily, the tubular prosthesis 180 are compressed in a radially compressed state within a delivery device. The tubular prosthesis 180 are positioned within the lumen of the stent 120. The tubular prosthesis 180 are partially deployed by removing the sheath or delivery device around the portion of the tubular prosthesis 180 which is positioned within the lumen of the stent 120. A secondary material is injected into the vicinity of the tubular prosthesis 180 and stent 120. The secondary material is allowed to react with the primary material 110 on the exterior surface of the tubular prosthesis 180 and the interior surface of the stent 120. The polymeric reaction product 130 from the two materials sealably secures the tubular prosthesis 180 to the stent 120. As above discussed separate delivery devices may be used to deploy each component of the prosthesis 100 or a multi-step delivery device may be used, as known in the art.

Figure 20:
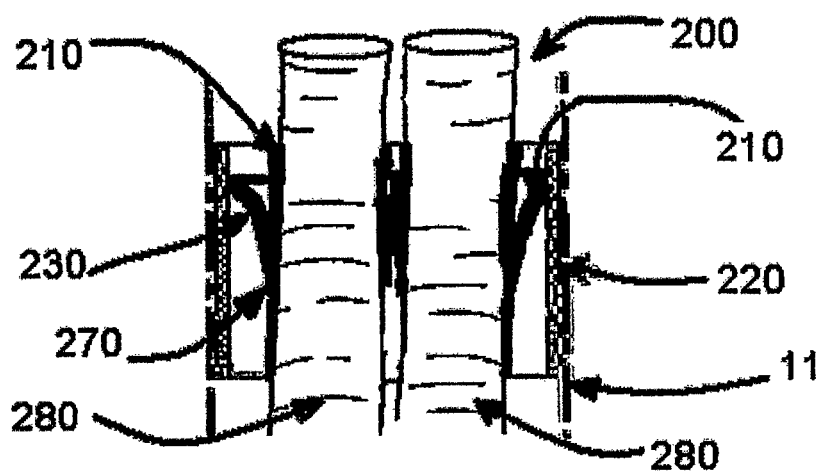
FIG. 20 is a plan view of an endovascular prosthesis of the present invention showing primary material on the membrane and grafts.
Figure 21:
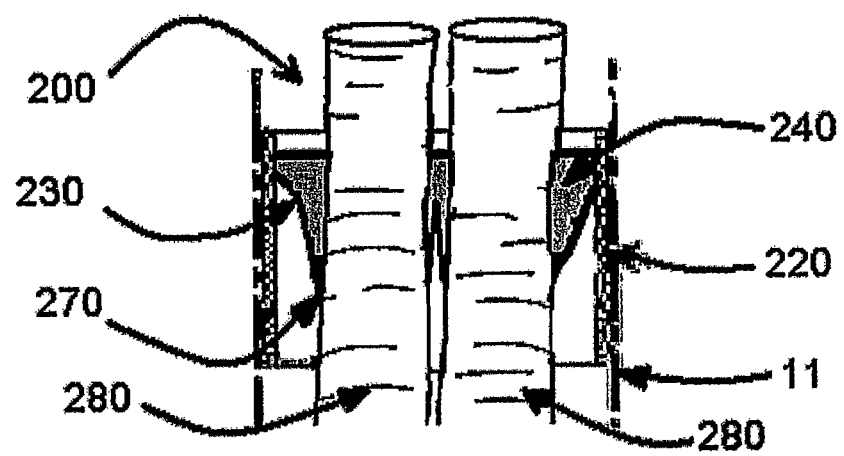
FIG. 21 shows the endovascular prosthesis of FIG. 20 showing the polymeric material sealably securing the tubular graft to a membrane.

In addition, combining the technology as shown in FIGS. 18 and 19 with the prosthesis 1 of FIG. 1, provides prosthesis 200 as shown in FIGS. 20 and 21. In this combination, the membrane 230 and the tubular prosthesis 280 are pretreated with the primary material 210, as described above. FIG. 20 shows tubular prosthesis 280 is placed within the stent lumen through the graft receiving member 270 of the membrane 230. A secondary material is introduced which reacts with the primary material 210 on the tubular prosthesis 280 and the membrane 230. A polymeric material 240 is formed which sealably secures the tubular prosthesis 280 to the stent 220, as shown in FIG. 21.

Prosthesis 200 is deployed in the same manner as discussed for prosthesis 100 of FIG. 18, except stent 120 is replaced with a first prosthesis 219 including a stent 220 and a membrane 230, attached to the stent 220, having graft receiving member 270. The first prosthesis 219 is deployed at the target site using a delivery device as above described. The tubular prosthesis 280 is compressed in a delivery device and then positioned through the graft receiving members 270. The tubular prosthesis 280 is deployed within the graft receiving members 270. A secondary reactive material is introduced in the vicinity of the membrane 230 and the tubular prosthesis 280. The secondary reactive material is allowed to react with the primary material 210 on the tubular prosthesis 280 and the membrane 230. The reaction product 240 results in a polymeric material which sealably secures the tubular prosthesis 280 to the membrane 230. Variations on this method may be used according to the known art.

Having described particular arrangements of the present invention herein, it should be appreciated by those skilled in the art that modifications may be made thereto without departing from the contemplated scope thereof. Accordingly, the arrangements described herein are intended to be illustrative rather than limiting, the true scope of the invention being set forth in the claims appended hereto.

What is claimed is:

1. An endovascular prosthesis comprising:
a first stent, the first stent comprising a first end, a second end, and an inner surface defining an inner lumen;
a first graft, the first graft comprising a first end, a second end, and an outer surface;
a first membrane, the first membrane being non-planar with a first end having a first width sufficient to extend across an entirety of the inner lumen of the first stent; a second end having a second width less than the first width where only the first end is engaged to the inner surface of the stent, the second end comprising a first peak formation comprising an apex, the apex comprising a first graft receiving member configured to receive a graft, wherein the first membrane is non-planar with and without a graft positioned within the first graft receiving member, the first membrane being engaged between the first and second ends of the first stent;
the first graft being positioned within the first graft receiving member, a first portion of the first peak formation conforming to a portion of the outer surface of the first graft, the apex of the first peak formation being closer to the first end of the first graft than the first portion of the first peak formation is to the first end of the first graft;
wherein the first end of the first stent, the first end of the first graft, and the apex of the first peak formation are directed in a first direction; the second end of the first stent and the second end of the first graft are directed in a second direction opposite the first direction, the first end of the first graft being closer to the apex of the first peak formation than the second end of the first graft.

2. The endovascular prosthesis of claim 1, the first stent having a longitudinal length greater than a longitudinal length of the first membrane.

3. The endovascular prosthesis of claim 1, the first graft having a longitudinal length greater than a longitudinal length of the first stent, wherein the second end of the first graft is a distance away from the first stent.

4. The endovascular prosthesis of claim 1, the first stent further comprising a graft engaged to an outer surface of the first stent.

5. The endovascular prosthesis of claim 1, the first peak formation further comprising a second portion, the second portion longitudinally adjacent to the first portion, the second portion being at an angle to the outer surface of the first graft, the first portion forming a majority of a longitudinal length of the first membrane.

6. The endovascular prosthesis of claim 1, the first stent being a tubular stent with a single opening at the distal end and a single opening at the proximal end.

7. The endovascular prosthesis of claim 1, the endovascular prosthesis further comprising a second graft, the second graft comprising a first end and having a second longitudinal length greater than a first longitudinal length of the stent;
the first membrane further comprising a second peak formation, the second peak formation comprising a first portion and an apex, the apex comprising a second graft receiving member;
the second graft being positioned within the second graft receiving member, the first portion of the second peak formation conforming to a portion of the second graft, the apex being closer to the first end of the second graft than the first portion of the first peak formation.

8. The endovascular prosthesis of claim 7, the first membrane further comprising a fluid flow opening.

9. The endovascular prosthesis of claim 8, the fluid flow opening being positioned between the first graft receiving member and the second graft receiving member.

10. The endovascular prosthesis of claim 8, the fluid flow opening being a slit, a hole, or a fluid penetrable material.

11. The endovascular prosthesis of claim 7, the first graft comprising a porous portion positioned a first distance away from the first stent, and the second graft comprising a porous portion positioned a second distance away from the first stent.

12. An endovascular prosthesis comprising:
a first stent the first stent comprising a first end a second end and an inner surface defining an inner lumen;
a first graft, the first graft comprising a first end, a second end, and outer surface;
a first membrane, the first membrane being non-planar with a first end having a first width sufficient to extend across an entirety of the inner lumen of the first stent; a second end having a second width less than the first width where only the first end is engaged to the inner surface of the stent, the second end comprising a first peak formation comprising an apex, the apex comprising a first graft receiving member configured to receive a graft, wherein the first membrane is non-planar with and without a graft positioned within the first graft receiving member;

the first graft being positioned within the first graft receiving member, a first portion of the first peak formation conforming to a portion of the outer surface of the first graft, the apex of the first peak formation being closer to the first end of the first graft than the first portion of the first peak formation is to the first end of the first graft;

the first graft further comprising a trunk, a first leg, and a second leg, the trunk forming the first end of the first graft, the first leg extending from the trunk and terminating in a second end, the second leg extending from the trunk and terminating in a third end, at least a portion of the trunk being positioned within the first graft receiving member and the first portion of the first peak formation conforming to a portion of the trunk.

13. An endovascular prosthesis comprising:

a stent comprising a distal end, a proximal end, a longitudinal length between the distal and proximal ends, an inner lumen; and a membrane supported by said stent, the membrane traversing the entire inner lumen, the membrane having a thickness less than the longitudinal length of the stent, the membrane being a non-planar disk with a first end wider than a second end, the membrane comprising:

a first peak formation and a first graft receiving member for sealably receiving a first tubular graft, the first peak formation having an apex, forming a part of the second end of the membrane first graft receiving member being positioned at the apex of the first peak formation, wherein at least a portion of the first peak formation is configured to conform to a portion of a first tubular graft in a sealable manner and the first graft receiving member is configured to be closer to an end of the first tubular graft than the first peak formation is to the end of the first tubular graft;

wherein the membrane is non-planar disk with and without a tubular graft positioned within the first graft receiving member;

a first tubular graft, the first graft sealably engaged to the first membrane at the first peak formation, the first tubular graft comprising a proximal end and a distal end, the proximal end of the first tubular graft being closer to the apex of the first peak formation and to the proximal end of the stent than the distal end of the first tubular graft;

wherein the proximal ends of the stent and the first tubular graft are directed in a proximal direction; the distal ends of the stent and the first tubular graft and directed in a distal direction; and the apex of the first peak formation is directed in the proximal direction.

14. The endovascular prosthesis of claim 13, the membrane further comprising:

a second peak formation and a second graft receiving member for sealably receiving a second tubular graft, the second peak formation having an apex, the second graft receiving member being positioned at the apex of the second peak formation, wherein at least a portion of the second peak formation is configured to conform to a portion of a second tubular graft in a sealable manner and the second graft receiving member is configured to be closer to an end of the second tubular graft than the second peak formation.

15. The endovascular graft of claim 14, further comprising:

a second graft, the second graft sealably engaged to the first membrane at the second peak formation.

* * * * *